US00PP23345P3

(12) United States Plant Patent
Tsukahara

(10) Patent No.: US PP23,345 P3
(45) Date of Patent: Jan. 22, 2013

(54) *PETUNIA* PLANT NAMED 'PDBZI934-0'

(50) Latin Name: ***Petunia* hybrid**
Varietal Denomination: PDBZI934-0

(75) Inventor: Jun Tsukahara, Yame (JP)

(73) Assignee: Daiichi Engei Co. Ltd. (JP)

( * ) Notice: Subject to any disclaimer, the term of this patent is extended or adjusted under 35 U.S.C. 154(b) by 0 days.

(21) Appl. No.: 12/930,843

(22) Filed: Jan. 19, 2011

(65) Prior Publication Data

US 2012/0185984 P1 Jul. 19, 2012

(51) Int. Cl.
*A01H 5/00* (2006.01)

(52) U.S. Cl. ..... Plt./356.12

(58) Field of Classification Search ..... Plt./356.12
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'PDBZI934-0' is disclosed, characterized by unique, fully double Red-Purple flowers with mounding to trailing plant habit. Plants of the new variety are highly floriferous with exceptionally good branching. The new variety is a *Petunia*, suitable as an outdoor garden or container plant.

1 Drawing Sheet

Latin name of the genus and species: *Petunia* hybrid.
Variety denomination: 'PDBZI934-0'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September 2006. The new variety was discovered in May of 2007 by the inventor in a group of seedlings resulting from that crossing, in a commercial greenhouse in Yame, Fukuoka, Japan.

Asexual reproduction of the new cultivar 'PDBZI934-0' by vegetative cuttings was first performed at a commercial greenhouse in Yame, Fukuoka, Japan in May 2007. Subsequently many generations have been produced and have shown that the unique features of this cultivar are stable and reproduced true to type.

SUMMARY OF THE INVENTION

The cultivar 'PDBZI934-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'PDBZI934-0'. These characteristics in combination distinguish 'PDBZI934-0' as a new and distinct *Petunia* cultivar:

1. Unique Red-Purple flower color.
2. Mounding and trailing plant shape.
3. Highly floriferous plant habit.
4. Fully double flowers.
5. Exceptionally good branching.

COMPARISON TO THE PARENT VARIETIES

Plants of the new cultivar 'PDBZI934-0' are similar in most horticultural characteristics to plants of the unnamed proprietary seed parent. However, the new variety has fully double flower whereas the seed parent does not have a fully double flower. Flower size of the new variety is larger than the seed parent. Additionally, plants of the seed parent produce Purple-Violet flowers, whereas 'PDBZI934-0' produces Red-Purple flowers.

Plants of the new cultivar 'PDBZI934-0' are similar in most horticultural characteristics to plants of the unnamed proprietary pollen parent. However, the pollen parent has Violet-Purple flowers, and does not produce fully double flowers.

COMPARISON TO COMMERCIAL VARIETIES

The new cultivar can be compared to the patented commercial variety 'KERPRILCOMP' U.S. Plant Pat. No. 19,327. 'PDBZI934-0' is similar to this commercial variety in most horticultural characteristics, including double flowering, however, plants of the new variety produce dark Red-Purple flowers, compared to the light purple flowers of 'KERPRILCOMP'. Additionally the new cultivar has a more mounding habit than 'KERPRILCOMP'.

BRIEF DESCRIPTION OF THE PHOTOGRAPH

The accompanying photograph in FIG. 1 illustrates in full color a typical plant of 'PDBZI934-0' grown in a greenhouse, in a 10 inch commercial basket. Age of the plant photographed is approximately 20 weeks from 5 rooted cuttings. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 edition, except where general terms of ordinary dictionary significance are used. The following observations and measurement describe 'PDBZI934-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Petunia* hybrid 'PDBZI934-0'.

PROPAGATION

Time to initiate roots: About 7 days at approximately 25° C.
Time to develop roots: About 14 to 21 days at approximately 25° C.
Root description: Fine, fibrous.

PLANT

Growth habit: Mounding to slightly trailing.
Age of the plant described: Approximately 20 weeks from 5 rooted cuttings.
Pot size of plant described: Approximately 10 inch basket.
Height: Approximately 20 cm from soil line to top of plant.
Plant spread: Approximately 55 cm at widest point.
Growth rate: Rapid.
Branching characteristics: Free branching.
Length of primary lateral branches: Approximately 17 cm.
Quantity of primary lateral branches: Approximately 60.
Characteristics of primary lateral branches:
- *Diameter*.—Approximately 0.3 cm.
- *Color*.—Near RHS Green 143B.
- *Texture*.—Pubescent.
- *Strength*.—Highly flexible, moderately strong.

Internode length: Approximately 1.7 cm.

FOLIAGE

Leaf:
- *Arrangement*.—Opposite.
- *Quantity*.—Approximately 20 per main lateral branch.
- *Average length*.—Approximately 3.5 cm.
- *Average width*.—Approximately 1.3 cm.
- *Shape of blade*.—Oblanceolate.
- *Apex*.—Acute.
- *Base*.—Obtuse.
- *Margin*.—Entire.
- *Texture of top surface*.—Matte with pubescence.
- *Pubescence*.—Very short, less than 1 mm hairs, densely covering leaf.
- *Aspect*.—Very slightly recurved.
- *Color*.—Young foliage upper side: Near RHS Green 137B. Young foliage under side: Near RHS Green 137C. Mature foliage upper side: Near RHS Green 137C. Mature foliage under side: Near RHS Green 137D.
- *Venation*.—Type: Pinnate. Venation color upper side: Near RHS Yellow-Green 144B. Venation color under side: Near RHS Yellow-Green 144C.
- *Petiole*.—Length: Approximately 0.2 cm. Diameter: Approximately 0.1 cm. Color: Near RHS Green 137C. Texture: Pubescent.

FLOWER

Natural flowering season: Spring and Summer.
Days to flowering from rooted cutting: Approximately 50.
Inflorescence and flower type and habit: Singly occurring at leaf axils, fully double flowers with fused petals.
Rate of flower opening: Approximately 3 to 5 days from bud to fully opened flower.
Flower longevity on plant: Approximately 1 week.
Approximate quantity of flowers per plant: Approximately 150 flowers and buds.
Flowers: Persistent.
Bud:
- *Shape*.—Oblong.
- *Length*.—Approximately 3 cm.
- *Diameter*.—Approximately 1.5 cm.
- *Color*.—Near RHS Purple 75B, distal end near Greyed-Purple 187A.

Flower size:
- *Diameter*.—Approximately 5 cm.
- *Length*.—Approximately 5 cm.
- *Flower measurements*.—Individual tube not measurable because filled with petals.
- *Petal quantity*.—Approximately 15, irregularly sized and fused.

Petals:
- *Width*.—Average 2.1 cm.
- *Quantity*.—15, fused.
- *Texture*.—Smooth.
- *Apex*.—Truncate.
- *Margin*.—Entire.

Color:
- *When opening*.—Inner surface: Near RHS Red-Purple 59B, near base Purple N79B. Outer surface: Near RHS Red-Purple 64C, near base Purple 79B.
- *Fully opened*.—Inner surface: Near RHS Red-Purple 64A, base near Red-Purple 71A. Outer surface: Near RHS Red-Purple 64A. Petal color, fading to: Near RHS Purple 79A, both surfaces.

Calyx/sepals:
- *Quantity per flower*.—5, fused at base.
- *Shape*.—Oblanceolate.
- *Length*.—Approximately 1.6 cm.
- *Width*.—Approximately 0.4 cm.
- *Apex*.—Obtuse.
- *Base*.—Fused.
- *Margin*.—Entire.
- *Texture*.—Pubescent.
- *Color*.—Upper Surface: Near RHS Green 137A. Lower Surface: Near RHS Green 137C.

Peduncle:
- *Length*.—Approximately 1.6 cm.
- *Diameter*.—Approximately 0.2 cm.
- *Color*.—Near RHS Green 144B.
- *Orientation*.—Approximately 45 degree angle from stem.

Fragrance: Sweet.

REPRODUCTIVE ORGANS

Stamens:
- *Number*.—5.
- *Filament length*.—Approximately 1.1 cm.

Anthers:
- *Length*.—Approximately 0.1 cm.
- *Shape*.—Oblate.
- *Color*.—RHS Greyed-Purple N186B.
- *Pollen*.—Not observed.

Pistil:

*Number*.—1.

*Length*.—Approximately 0.3 cm.

*Style*.—Length: Approximately 0.6 cm. Color: Near RHS White N155C.

*Stigma*.—Shape: Globular. Color: Near RHS Greyed-Purple N186B. Ovary Color: Near RHS Yellow-Green 145A.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° to 35° C.

What is claimed is:

1. A new and distinct cultivar of *Petunia* plant named 'PDBZI934-0' as herein illustrated and described.

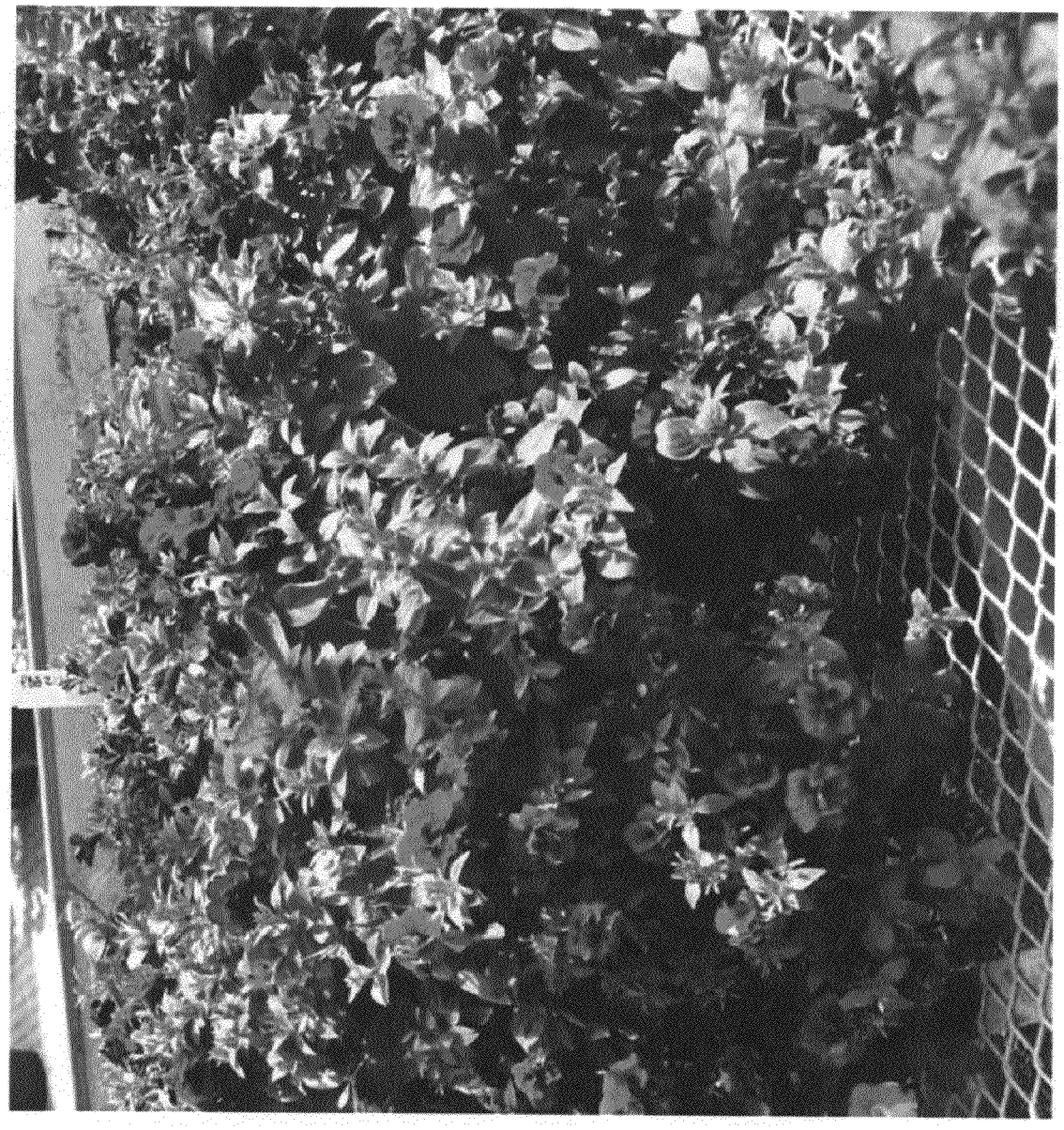

* * * * *